United States Patent [19]
Karppanen et al.

[11] Patent Number: 4,931,305
[45] Date of Patent: Jun. 5, 1990

[54] MIXTURE OF SALTS AND USES OF THE MIXTURE

[75] Inventors: Heikki Karppanen; Pirjo L. Karppanen, both of Helsinki, Finland

[73] Assignee: Pharmaconsult OY, Finland

[21] Appl. No.: 273,186

[22] Filed: Nov. 16, 1988

Related U.S. Application Data

[63] Continuation of Ser. No. 35,239, Apr. 6, 1987, abandoned, which is a continuation of Ser. No. 760,741, filed as PCT FI84/00084 on Nov. 21, 1984, published as WO85/02324 on Jun. 6, 1985, abandoned.

[30] Foreign Application Priority Data

Nov. 24, 1983 [FI] Finland .................................. 834309

[51] Int. Cl.$^5$ ............................................. A23L 1/237
[52] U.S. Cl. ..................................................... 426/649
[58] Field of Search ......................................... 426/649

[56] References Cited

U.S. PATENT DOCUMENTS 4,473,595 9/1984 Rood et al. .......................... 426/649

FOREIGN PATENT DOCUMENTS 621230 11/1935 Fed. Rep. of Germany .
2305980 2/1973 Fed. Rep. of Germany .
81522 3/1985 Norway .
363465 2/1969 Sweden .
73025918 3/1982 Sweden .
2015863B 12/1982 United Kingdom .

Primary Examiner—Joseph Golian
Attorney, Agent, or Firm—Burns, Doane, Swecker & Mathis

[57] ABSTRACT

Mixture of salts that contains dissociable ions of Mg, K, Na or H. The mixture can be used as table salt or preservative salt, such as fruit salts, as baking powder, or as a preparation that maintains health.

5 Claims, No Drawings

MIXTURE OF SALTS AND USES OF THE MIXTURE

This application is a continuation of application Ser. No. 07/035,239, filed Apr. 6, 1987, now abandoned, which is a continuation of application Ser. No. 760,741, filed as PCT FI84/00084 on Nov. 21, 1984, published as WO85/02324 on June 6, 1985, now abandoned.

The present invention is concerned with a mixture of salts that can be used as an additive for food, as a preservative, as fruit salts, as baking powder, or as a preparation maintaining health.

It is well known that today, man obtains an excess of calcium and especially of sodium but too little potassium and magnesium from food. This causes conditions of excess or deficiency, of even diseases, such as stroke, hypertension, cardiac arrhythmias, and even sudden deaths of cardiac origin.

Diuretic drugs are widely used for the treatment of hypertension. They decrease the body-burden of sodium by increasing its excretion into the urine. They, however, increase also the excretion of potassium, magnesium and hydrogen ions. The diazide diuretics, which are the most widely used, decrease simultaneously the excretion of calcium. This, especially together with the unbalanced supply of sodium, calcium, potassium and magnesium, often causes deficiency of potassium or magnesium, deficiency of hydrogen ions, i.e. alkalosis, and excessive and harmful increase of calcium.

The alkalosis is especially harmful because it further decreases the already too small concentrations of potassium and magnesium in plasma and other extracellular fluids. The decrease in the concentrations of potassium, magnesium, and hydrogen ions and the increase in the concentration of calcium in plasma and other extracellular fluids further increase the occurrence of cardiac arrhythmias, and the risk of myocardial damage, e.g., heart infarcts.

Administration of potassium alone has, however, not proved efficient, e.g., for the prevention of cardiac arrhythmia, especially if the patient also suffers from magnesium deficiency at the same time. The administration of potassium alone has been even found to increase the deficiency of magnesium with its harmful effects. Administration of magnesium alone may, on the other hand, cause even detrimental reduction in the potassium concentration outside the cells when the sodium-potassium-ATPase, activated by the increased magnesium, transfers potassium into the cells. Moreover, an abundant supply of sodium increases the excretion of potassium and magnesium into the urine.

Even potassium and magnesium together may be ineffective in preventing cardiac arrhythmias and damage of the cardiac muscle if the patient suffers from alkalosis at the same time. The alkalosis may become even worse, because many physiologically usable potassium or magnesium salts have an alkalizing effect.

An increase in the concentration of hydrogen ions alone causes a detrimentally extensive reduction in the quantities of potassium and magnesium inside the cells unless a sufficient quantity of potassium and magnesium is available to the extracellular space from the alimentary tract.

It is known to try to correct the excessive supply of sodium by using mixtures of salts in which sodium has been partly or wholly replaced by other substances, which tend to mimic the taste of the sodium salt. Potassium or calciums salts have been generally used as the substituting substances. The use of calcium salts is not, however, reasonable, as it further increases the already too high body-burden of calcium. Potassium salts alone, on the other hand, have often been found to exert a bitter and unpleasant aftertaste.

In the Patent Publication FI No. 60,107 (corresponds to the Patent Publication GB No. 2,015,863B), a mixture of salts is suggested that contains 50 to 65 per cent by weight of sodium chloride, 20 to 40 per cent by weight of potassium chloride, and 5 to 20 per cent by weight of magnesium chloride or sulphate. By using this mixture instead of the normal table salt, it is possible to reduce the supply of sodium and to increase the supply of potassium and magnesium. However, this composition of salts is not satisfactory, because the quite crucial role of the hydrogen ions in the potassium and magnesium metabolism has not been recognized. Besides, in the salt composition of FI No. 60,107 it is necessary to use magnesium sulphate or chloride hydrate. This is because most of the other magnesium salts are not soluble enough in water. Magnesium chloride is extremely hygroscopic, and magnesium sulphate easily liberates its crystal water in warm conditions. That is why the mixture easily gets moist and cloggy.

The object of the invention has been to create a salt composition, which, in a natural way, prevents the drawbacks of the unbalanced supply of sodium, calcium, potassium, and magnesium and the harms of certain diuretic drugs, but the taste and physical properties of which, on the other hand, are accepted by man.

Now, a mixture of physiologically usable compounds has been discovered, which contains both magnesium, potassium, sodium, and hydrogen ions as dissociable cations. The quantity of magnesium ions is 1 to 80 %, that of potassium ions 2 to 90 %, that of sodium ions 0 to 80 %, and that of hydrogen ions 0.5 to 80 % of the overall molar quantity of the said ions. By means of the use of the mixture of salts thus discovered instead of table salt or known salt compositions, it is possible to prevent drawbacks resulting within the electrolyte balance of the body from unbalanced food, from separate dosage of the substances and from the medical treatment with diuretics and, moreover, to increase the concentration of hydrogen ions in the body in alkalosis.

It has also been found that the invented composition has additionally some quite unexpected properties.

When the so called spontaneously hypertensive rats are fed on dry food containing 8 % sodium chloride, the blood pressure of the rats increases strongly, and the rats die early of stroke apolexy. When the same amount of the now invented mixture is used instead of sodium chloride, the blood pressure also increases, but not as much as when sodium chloride is used. The rats, however, totally unexpectedly remain healthier and live even longer than the rats with lower pressure which are fed on food of low salt content. The reactions of the spontaneously hypertensive rats have proved to be good models also in the research of hypertension in man. Therefore it is to be expected that the mixture will produce the same effects also in man.

The preservative properties of the now invented mixture of salts have proved to be better than those of other mixtures containing potassium and magnesium. It is also possible to reduce the overall salt quantity required for the preservation, because the reduced pH further improves the preservation quality.

In the now invented salt compositions it is also possible to use magnesium compounds, such as magnesium oxide or carbonate, which are soluble only in acidic medium. Thus it is possible to avoid the use of magnesium sulphate or chloride, and to make compositions usable also in warm and humid climatic conditions.

It has also been noticed that acids and acidic salts intensify the salty taste of the mixture. This also reduces the requirement of using sodium.

Because of their better healthy the now invented salt compositions are also more acceptable than the common table salt or salt mixtures in the delivery of trace elements, such as iodine, fluorine, copper, selenium, chromium, zinc, iron, etc. or vitamines to whole groups of populations. The solubility of many trace element compounds will be increased, which will also increase their biological availability.

In the mixture, usable magnesium compounds are in particular magnesium sulphate, magnesium oxide, and magnesium carbonate, but also many other compounds are possible. Suitable potassium compounds are, e.g., potassium carbonate, potassium bitartrate, potassium-sodium tartrate, as well as, in particular, potassium chloride and potassium bicarbonate. Sodium compounds that may be concerned are, e.g., sodium glutamate, sodium citrate, as well as, in particular, sodium chloride and sodium bicarbonate. As compounds that deliver hydrogen ions, it is possible to use in particular lysine hydrochloride, tartaric acid, and citric acid. Further compounds that may be concerned are, among others, benzoic acid, sorbic acid, ascorbic acid, and glutamic acid hydrochloride, as well as some other acidic amino acids and their salts.

The mixture in accordance with the invention can be used as a food additive replacing sodium chloride as table salt, as a preservative, as fruit salts, as baking powder, or as a preparation maintaining health.

In an appropriate preparation of table salt, the quantity of magnesium ions is 1 to 30% (in particular 2 to 15 %), that of potassium ions 10 to 80% (in particular 15 to 40 %), that of sodium ions 15 to 90 % (in particular 50 to 80 %), and that of hydrogen ions 0.5 to 20 % (in particular 1 to 5 %). Two of the preferred rations are given in Examples 1 and 2.

In particular as a preservative, it is possible to use a mixture which contains 2 to 20 % of magnesium ions, 15 to 40 % of potassium ions, 40 to 70 % of sodium ions, and 5 to 20 % of hydrogen ions. One of the preferred compositions will be given in Example 3.

In particular a fruit salts preparation contains 3 to 80 % of magnesium ions, 4 to 90 % of potassium ions, 0 to 80 % of sodium ions, and 2 to 80 % of hydrogen ions. The mixture includes some fruit acid of agreeable taste, e.g. 2 to 75 % of the overall molar quantity of the above cations, and preferably also bicarbonate ions, whereat the solution becomes a bubbling drink of fresh taste. A typical fruit salts preparation will be described in Example 4.

A baking powder in accordance with the invention contains 4 to 80 % of magnesium ions, 4 to 80 % of potassium ions, 5 to 90 % of sodium ions, and 0.5 to 40 % of hydrogen ions. Moreover, the mixture must include bicarbonate ions, from which the carbon dioxide is liberated and raises the dough. Example 5 describes a preferred mixture of baking powder.

A preparation maintaining the health and inhibiting a disturbance of the electrolyte balance contains 2 to 90% of magnesium ions, 2 to 90% of potassium ions, 0 to 70% of sodium ions, and 1.5 to 80% of hydrogen ions. The examples 6 and 7 describe some preferred mixtures.

EXAMPLE 1

Table salt preparation

| | |
|---|---|
| MgSO.7H$_2$O | 12 g |
| KCl | 28 g |
| NaCl | 58 g |
| Lysine.HCl | 2 g |

(Mole ratio Mg:K:Na:H is about 3:26:69:1)

EXAMPLE 2

Table salt preparation

| | |
|---|---|
| MgCO$_3$ | 1 g |
| MgO | 2 g |
| KCl | 25 g |
| NaCl | 60 g |
| Tartaric acid | 10 g |
| Lysine.HCl | 2 g |

(Mole ratio Mg:K:Na:H is about 4:21:66:9)

EXAMPLE 3

Preservative salt

| | |
|---|---|
| MgCl$_2$.6H$_2$O | 9 g |
| KCl | 21 g |
| NaCl | 50 g |
| Benzoic acid | 20 g |

(Mole ratio Mg:K:Na:H is about 4:24:58:14)

EXAMPLE 4

Fruit salts

| | |
|---|---|
| MgO | 2 g |
| KHCO$_3$ | 20 g |
| NaHCO$_3$ | 20 g |
| Na$_2$CO$_3$ | 3 g |
| K—Na-tartrate | 1 g |
| Citric acid | 27 g |
| Tartaric acid | 27 g |

(Mole ratio Mg:K:Na:H is about 4:16:21:60)

EXAMPLE 5

Baking powder

| | |
|---|---|
| MgO | 20 g |
| KHCO$_3$ | 60 g |
| NaHCO$_3$ | 10 g |
| Lysine.HCl | 10 g |

(Mole ratio Mg:K:Na:H is about 39:47:9:4)

EXAMPLE 6

Mixture that maintains health, for tablets or capsules

| | |
|---|---|
| MgO | 28.5 g |
| KCl | 52.7 g |
| NH$_4$Cl | 18.8 g |

(Mole ratio Mg:K:H is 40:40:20)

EXAMPLE 7

Mixture that maintains health, for effervescent tablets or dose powders

| | |
|---|---|
| MgO | 9 g |
| KCl | 8 g |
| KHCO$_3$ | 16 g |
| Citric acid | 67 g |

(Mole ratio Mg:K:H is about 28:3:39)

What is claimed is:

1. A salt substitute composition consisting essentially of magnesium sulfate, potassium chloride, sodium chloride and acidic amino acid or acidic acid salt thereof, the ratio of the respective ingredients on a molar bases being 3:26:69:to 4:21:66:9.

2. The composition as claimed in claim 1, wherein the acidic amino acid or acidic acid salt thereof is in the form of an acidic salt of an amino acid.

3. The composition as claimed in claim 2, wherein said acidic salt is in the form of an acidic salt of lysine.

4. The composition as claimed in claim 3, wherein said acidic salt of lysine is lysine hydrochloride.

5. A salt substitute composition comprising magnesium sulfate, potassium chloride, sodium chloride and of an acidic salt of lysine, the ratio of the respective ingredients on a molar basis being 3:26:69:1.

* * * * *